US008158371B2

(12) United States Patent
Collins et al.

(10) Patent No.: US 8,158,371 B2
(45) Date of Patent: Apr. 17, 2012

(54) **ASSAY FOR ANTIBODIES TO *MYCOBACTERIUM PARATUBERCULOSIS***

(75) Inventors: Michael T. Collins, Blue Mounds, WI (US); Sung Jae Shin, Madison, WI (US); Donghee Cho, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 12/904,790

(22) Filed: Oct. 14, 2010

(65) Prior Publication Data

US 2011/0027812 A1    Feb. 3, 2011

Related U.S. Application Data

(62) Division of application No. 11/850,282, filed on Sep. 5, 2007, now abandoned.

(60) Provisional application No. 60/843,110, filed on Sep. 8, 2006.

(51) Int. Cl.
*G01N 33/53* (2006.01)
*C12N 1/20* (2006.01)
*A61K 39/04* (2006.01)

(52) U.S. Cl. ..... 435/7.1; 435/41; 435/252.3; 424/130.1; 424/184.1; 424/200.1; 424/234.1; 424/248.1

(58) Field of Classification Search ............... 424/130.1, 424/184.1, 200.1, 234.1, 248.1; 435/7.1, 435/41, 252.3
See application file for complete search history.

(56) References Cited

U.S. PATENT DOCUMENTS

| 3,791,932 | A |  | 2/1974 | Schuurs et al. |
| 3,875,011 | A |  | 4/1975 | Rubenstein et al. |
| 3,879,262 | A |  | 4/1975 | Schuurs et al. |
| 4,256,834 | A |  | 3/1981 | Zuk et al. |
| 4,261,968 | A |  | 4/1981 | Ullman et al. |
| 4,490,473 | A |  | 12/1984 | Brunhouse |
| 6,221,364 | B1 | * | 4/2001 | Pavelka et al. ............. 424/248.1 |

FOREIGN PATENT DOCUMENTS

| EP | 1780547 A1 | 5/2007 |
| WO | WO9734149 A1 | 9/1997 |
| WO | WO2008030865 A1 | 3/2008 |

OTHER PUBLICATIONS

Cho, et al., Proteomic Identification of Immunogenic *Mycobacterium paratuberculosis* Proteins, Eighth International Colloquium on *paratuberculosis*, Copenhagen, Denmark, Aug. 14-17, 2005, MT XP002464448 [Abstract].
Cho, et al., Identification of Proteins of Potential Diagnostic Value for Bovine *paratuberculosis*, Proteomics 6 (21):5785-5794, Oct. 2006.
Cho, et al., Comparison of the Proteosomes and Antigenicities of Secreted and Cellular Proteins Produced by *Mycobacterium paratuberculosis*, Clin. Vaccine Immunol. 13(10):1155-1161, Oct. 2006.
Choudhry, et al., Detection of Mycobacterium Tuberculosis Antigens in Urinary Proteins of Tuberculosis Patients, Eur. J. Clin. Microbiol. Infect. Dis 21:1-5, 2002.
Collins, et al., Evaluation of Five Antibody Detection Tests for Diagnosis of Bovine *paratuberculosis*, Clin. Diagn. Lab. Immunol. 12(6):685-692, 2005.
Gardner, et al., Receiver-operating Characteristic Curves and Likelihood Ratios: Improvements Over Traditional Methods for the Evaluation and Application of Veterinary Clinical Pathology Tests, Vet. Clin. Pathol. 35(1):8-17, 2006.
Glickman, et al., Rapid Identification of Mycolic Acid Patterns of *Mycobacteria* by High-Performance Liquid Chromatography Using Pattern Recognition Software and a *Mycobacterium* Library, J. Clin. Microbiol. 32(3):740-745, 1994.
Greenwood, et al., The Preparation of (131)I-Labelled Human Growth Hormone of High Specific Radioactivity, Biochem. J. 89:114-123, 1963.
Harlow, et al., Labeling Antibodies with Iodine, CSH Protocols, doi:10.1101/pdb.prot4287, 2006.
Kaufman, et al., Handbook of Molecular and Cellular Methods in Biology and Medicine, CRC Press, Boca Raton, FL, 1995.
Miller, A Short Course in Bacterial Genetics, Cold Spring Harbor Laboratory Press, Cold Spring Harbor, NY, 1992.
Pereira, et al., Development of Antigen Detection Assay for Diagnosis of Tuberculosis Using Sputum Samples, J. Clin. Microbiol. 38(6):2278-2283, 2000.
Sambrook, et al., Molecular Cloning: A Laboratory Manual, 3rd ed., Cold Spring Harbor Laboratory Press, Cold Spring Harbor, NY, 2001.
Shin, et al., Diagnosis of Bovine *paratuberculosis* by a Novel Enzyme-Linked Immunosorbent Assay Based on Early Secreted Antigens of *Mycobacterium avium* Subsp. *paratuberculosis*, Clin. Vaccine Immunol. 15(8):1277-1281, 2008.
Shin, et al., Rapid *Mycobacterial* Liquid Culture-Screening Method for *Mycobacterium avium* Complex Based on Secreted Antigen-Capture Enzyme-Linked Immunosorbent Assay, Clin. Vaccine Immunol. 16(5):613-620, 2009.
Singer, et al., Genes and Genomes: A Changing Perspective, University Science Books, Mills Valley, CA, 1991.
Sung, et al., Variation in Resistance of *Mycobacterium paratuberculosis* to Acid Environments as a Function of Culture Medium, Appl. Environ. Microbiol. 69(11):6833-6840, 2003.
Sung, et al., Possible Association of GroES and Antigen 85 Proteins with Heat Resistance of *Mycobacterium paratuberculosis*, Appl. Environ. Microbiol. 70(3):1688-1697, 2004.
Sweeney, et al., Longitudinal Study of ELISA Seroreactivity to *Mycobacterium avium* Subsp. *paratuberculosis* in Infected Cattle and Culture-Negative Herd Mates, J. Vet. Diagn. Invest. 18:2-6, 2006.
PCT International Preliminary Report on Patentability, PCT/US2007/077625, Mar. 19, 2009.

(Continued)

*Primary Examiner* — Rodney P. Swartz
(74) *Attorney, Agent, or Firm* — Quarles & Brady LLP

(57) ABSTRACT

A method of detecting an immune response to a paratuberculosis-specific antigen, comprising incubating a sample from a subject with the paratuberculosis-specific antigen and detecting the presence of an antibody in the sample as an indication of an immune response to the paratuberculosis-specific antigen. The antigen may be obtained from a novel *M. paratuberculosis* strain JTC303. The antigen may be obtained from the JTC303 culture filtrate. Also provided are antibodies to the paratuberculosis-specific antigen, and a diagnostic kit for the detection of an immune response to a paratuberculosis-specific antigen in a mammal.

**

OTHER PUBLICATIONS

PCT International Search Report, PCT1US2009/037469, Jul. 15, 2009.
United States Patent and Trademark Office, Office Action Summary and Detailed Action, U.S. Appl. No. 11/850,252, Jun. 24, 2008.
Response to Restriction/Election Requirement, U.S. Appl. No. 11/850,282, Jul. 24, 2008.
United States Patent and Trademark Office, Office Action Summary and Detailed Action, U.S. Appl. No. 11/850,282, Sep. 19, 2008.
Amendment and Request for Reconsideration, U.S. Appl. No. 11/850,282, Jan. 7, 2009.
United States Patent and Trademark Office, Office Action Summary and Detailed Action, U.S. Appl. No. 11/850,282, Apr. 30, 2009.
Amendment and Request for Reconsideration, U.S. Appl. No. 11/850,282, Jun. 30, 2009.
United States Patent and Trademark Office, Interview Summary, U.S. Appl. No. 11/850,282, Jul. 1, 2009.
United States Patent and Trademark Office, Office Action Summary and Detailed Action, U.S. Appl. No. 11/850,282, Jul. 10, 2009.
Amendment and Request for Reconsideration, U.S. Appl. No. 11/850,282, Oct. 12, 2009.
United States Patent and Trademark Office, Office Action Summary and Detailed Action, U.S. Appl. No. 11/850,282, Jan. 22, 2010.
Amendment in Response to Final Office Action, U.S. Appl. No. 11/850,282, Mar. 22, 2010.
United States Patent and Trademark Office, Office Action Summary and Detailed Action, U.S. Appl. No. 11/850,282, Apr. 5, 2010.
United States Patent and Trademark Office, Office Action Summary and Detailed Action, U.S. Appl. No. 11/850,282, May 17, 2010.
United States Patent and Trademark Office, Interview Summary, U.S. Appl. No. 11/850,282, Oct. 13, 2010.
Response to Non-Final Office Action, U.S. Appl. No. 11/850,282, Oct. 14, 2010.
United States Patent and Trademark Office, Office Action Summary and Detailed Action, U.S. Appl. No. 11/850,282, Nov. 2, 2010.
Intellectual Property Office of New Zealand, Examination Report, Patent Application No. 575023, Jun. 30, 2010.
United States Patent and Trademark Office, Office Action Summary and Detailed Action, U.S. Appl. No. 12/406,253, Feb. 7, 2011.
Applicant, Response to Restriction Requirement, U.S. Appl. No. 12/406,253, Mar. 4, 2011.

* cited by examiner

ASSAY FOR ANTIBODIES TO *MYCOBACTERIUM PARATUBERCULOSIS*

CROSS-REFERENCE TO RELATED APPLICATIONS

This application is a divisional application of U.S. patent application Ser. No. 11/850,282, filed Sep. 5, 2007 which claims the benefit of U.S. Provisional Patent Application Ser. No. 60/843,110, filed Sep. 8, 2006, both of which are incorporated by reference in their entirety for all purposes.

STATEMENT REGARDING FEDERALLY SPONSORED RESEARCH OR DEVELOPMENT

This invention was made in part with United States government support awarded by the USDA/CSREES grant 00-35204-9311. The United States may have certain rights in this invention.

FIELD OF THE INVENTION

This invention relates to the field of diagnostic assays. More particularly, the invention provides novel antigen preparations, kits, and methods that can be used in an assay for antibodies to *Mycobacterium paratuberculosis*.

BACKGROUND

*Mycobacterium avium* subspecies *paratuberculosis* (hereinafter referred to as *M. paratuberculosis*) causes Johne's disease (paratuberculosis) in dairy cattle and other animals characterized by chronic diarrhea, weight loss, and malnutrition, resulting in estimated losses of $220 million per year in the U.S.A. alone. World-wide, the prevalence of the disease can range from as low as 3-4% of the examined herds in regions with low incidence (such as England), to high levels of 50% of the herds in some areas within the U.S.A. (Wisconsin and Alabama). Cows with Johne's disease excrete *Mycobacterium paratuberculosis* in their milk. In humans, *M. paratuberculosis* bacilli have been found in tissues examined from Crohn's disease patients indicating possible zoonotic potential of this pathogen.

Diagnosis of bovine paratuberculosis is difficult, and is typically accomplished by detecting either the causative agent *M. paratuberculosis* or an immune response to the agent. Many clinical methods for detecting and identifying *Mycobacterium* species in samples require analysis of the bacterium's physical characteristics, physiological characteristics, or biochemical characteristics. These methods require relatively high concentrations of bacteria in the sample to be detected, may be subjective depending on the clinical technician's experience and expertise, and are time-consuming. Because *Mycobacterium* species are often difficult to grow in vitro and may take weeks to reach a useful density in culture, these methods can also result in delayed diagnosis and intervention to stop the spread of infection. For example, microbiological culture of *Mycobacterium* from feces is a widely used diagnostic test; however, this assay requires up to 16 weeks for completion.

Commercially available diagnostic tests exist. For example, serologic tests based on Enzyme-Linked Immunoabsorbent Assay (ELISA) technology are popular commercially available immunoassays. ELISA technology is based upon the use of an enzyme-linked antibody marker to detect the presence of specimen antibody bound to a known antigen that is attached to a solid support. However, the accuracy of existing commercially available ELISA kits for bovine paratuberculosis is relatively poor. A comparison of commercial ELISA kits showed that assays performed comparably overall with diagnostic sensitivity ranging from 27.9% to 44.5% for fecal culture-positive cattle (Collins et al., 2005, *Clin. Diagn. Lab. Immunol.* 12: 685-692). In a more recent study, the commercially-available ELISAs for *M. paratuberculosis* were found to have an even lower sensitivity of approximately 13.5% (Sweeney et al., 2006, *J. Vet. Diagn. Invest.* 18: 2-6). Accordingly, there is a need in the art for paratuberculosis diagnostic tests based on immune response detection.

BRIEF SUMMARY

This invention relates to the field of diagnostic assays. More particularly, the invention provides compositions and methods for the detection of paratuberculosis in mammals.

This invention provides an isolated *Mycobacterium paratuberculosis* strain JTC303, deposited as PTA-7788 with the American Type Culture Collection (ATCC) on Aug. 15, 2006. Also provided are isolated mutants of JTC303.

The present invention provides antigens isolated from *M. paratuberculosis* strain JTC303 and the mutant strains derived there from. These antigens may be obtained from the bacterial cell homogenate, i.e. cellular extract (CE). In preferred embodiments, the antigens are obtained from the JTC303 culture filtrate (CF).

The present invention provides paratuberculosis-specific antibodies and antibody fragments. The antibodies may be specific for antigens obtained from the *M. paratuberculosis* strain JTC303. Preferably, the antibodies may be specific for antigens obtained from the *M. paratuberculosis* strain JTC303 culture filtrate. The paratuberculosis-specific antibodies or antibody fragments may be monoclonal, polyclonal, labeled, etc.

The present invention provides absorption antigens that may be mixed with the sample to remove nonspecific antibodies. These antigens may be derived from the cellular extracts (CE) of mycobacteria. The antigens may be added as antigen preparations. Absorption antigens are preferably obtained from cellular extracts of *Mycobacterium phlei*. In alternative preferred embodiments, absorption antigens are obtained from cellular extracts of *Mycobacterium terrae*.

Also provided is a method of diagnosing paratuberculosis in a subject, including contacting a sample from said subject with a culture filtrate obtained from *M. paratuberculosis* strain JTC303, and assaying for the presence or absence of an antibody in said sample by detecting specific binding of said antibody or fragment thereof, where the presence of an antibody indicates that said subject has paratuberculosis. The diagnostic method may be an enzyme-linked immunosorbent assay (ELISA) or anyone of several other antibody detection technologies such as agar-gel immunodiffusion, complement fixation, etc.

Diagnosis of paratuberculosis may be performed using a variety of types of mammalian samples including serum or milk. The samples may be clinical samples. The mammal sampled may be human or it may be animal, e.g. bovine.

The invention also provides a diagnostic kit for the detection of an immune response to a paratuberculosis-specific antigenic preparation in a subject, which may include a paratuberculosis-specific antigen from *M. paratuberculosis* strain JTC303 and an anti-bovine immunoglobulin antibody. The anti-bovine immunoglobulin antibody may be labeled. The kit may also include an absorbing antigen preparation.

The kit may include a container for incubating the paratuberculosis-specific antigen with a sample from the subject.

DETAILED DESCRIPTION OF THE PRESENTLY PREFERRED EMBODIMENTS

Figure 1:
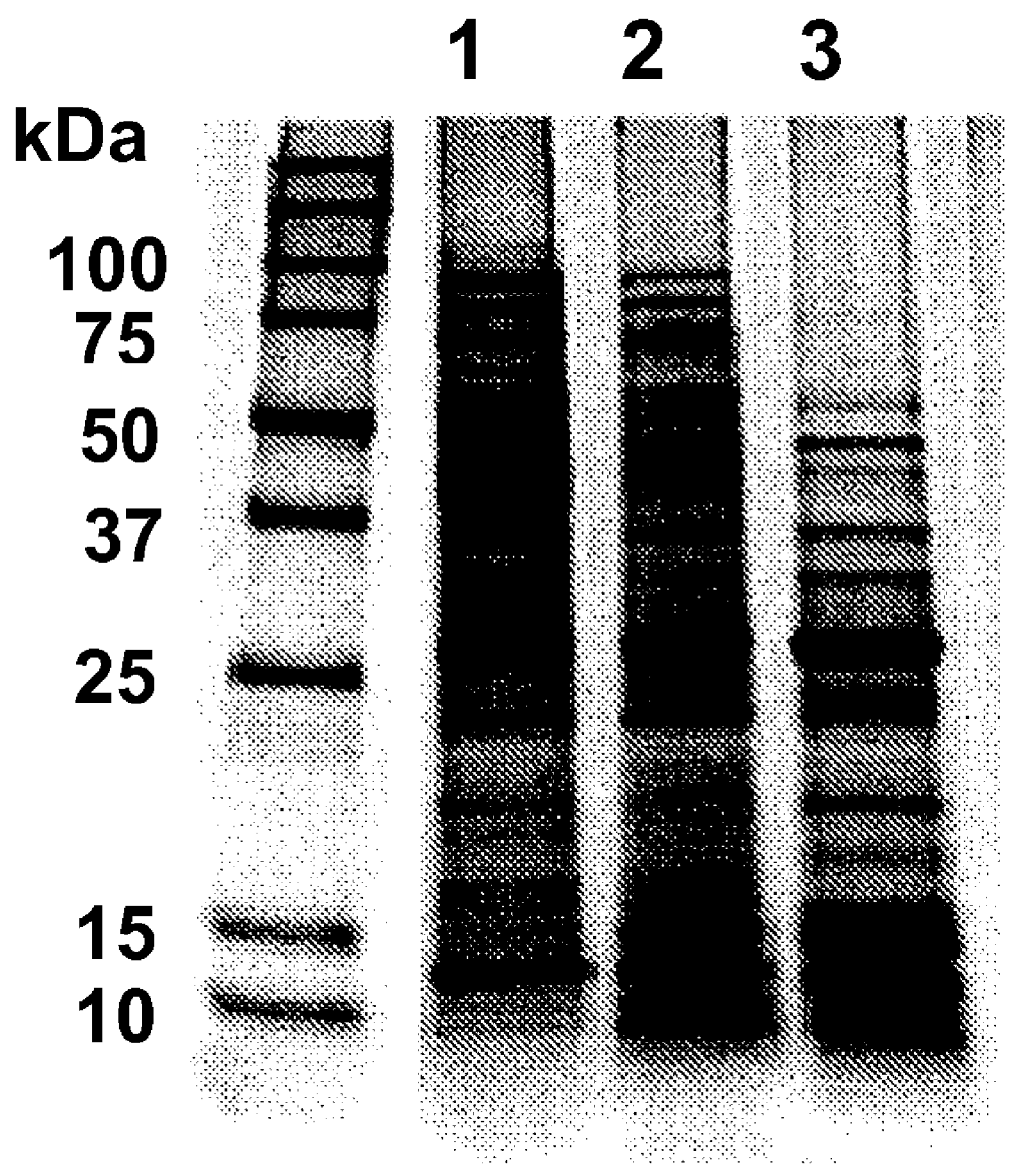
FIG. 1 is an image showing SDS-PAGE results from cellular extract proteins (lanes 1 and 2) and from culture filtrate proteins (lane 3).
Figure 2:
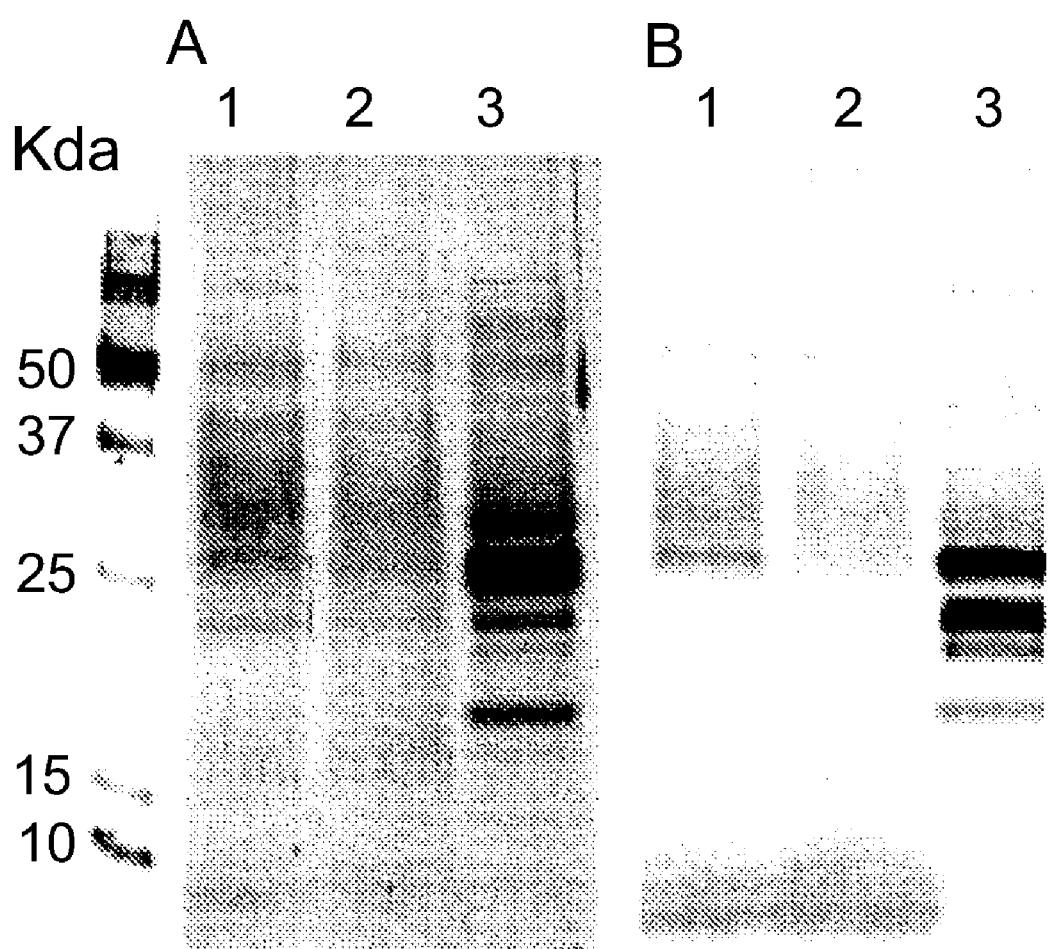
FIG. 2 shows images of immunoblots from cellular extract proteins (lanes 1 and 2) and from culture filtrate proteins (lane 3), before (A) and after (B) serum preabsorption using *M. phlei*.
Figure 3:
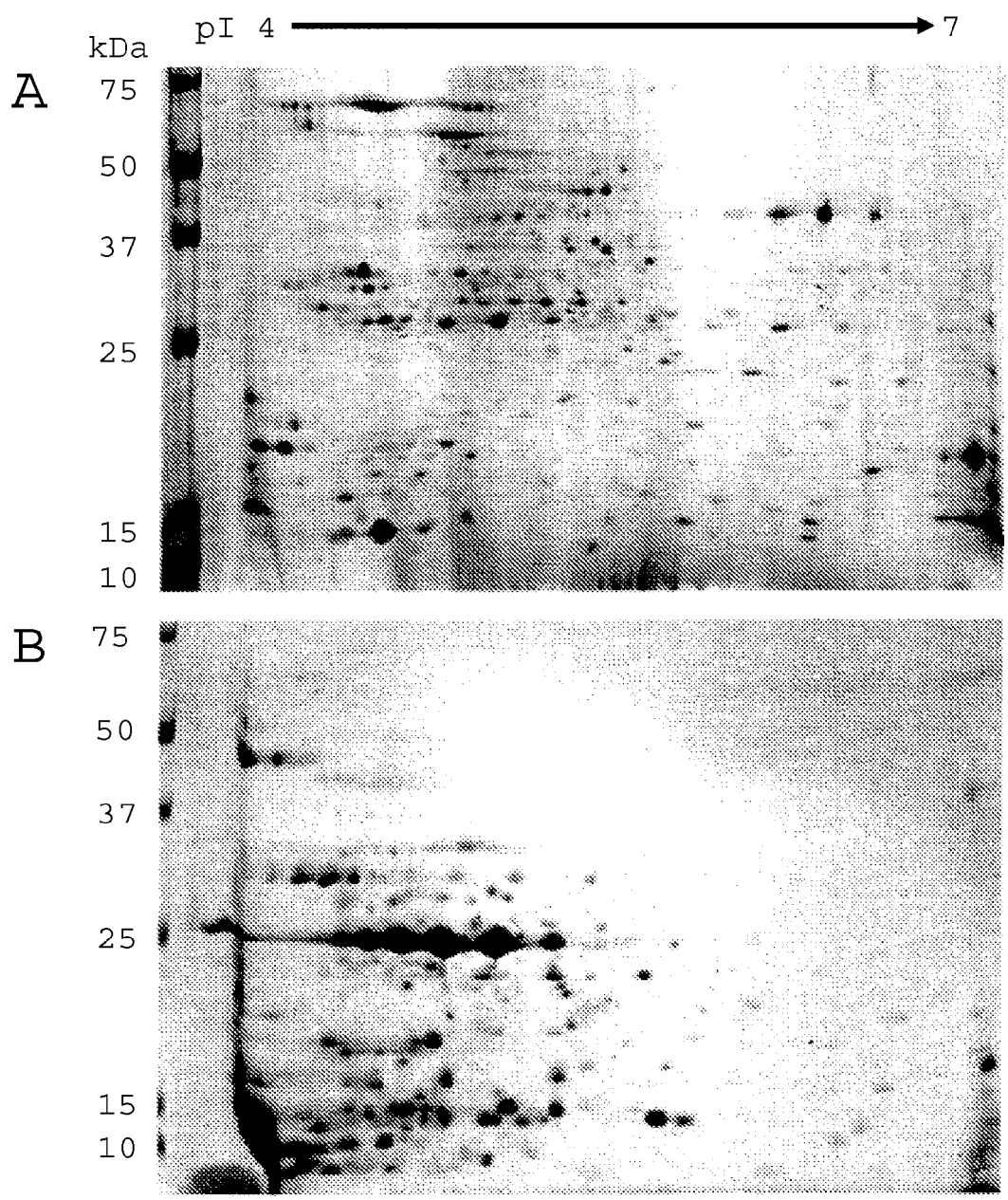
FIG. 3 shows images of cellular extract proteins (A) and culture filtrate proteins (B) separated using IEF SDS-PAGE.
Figure 4:
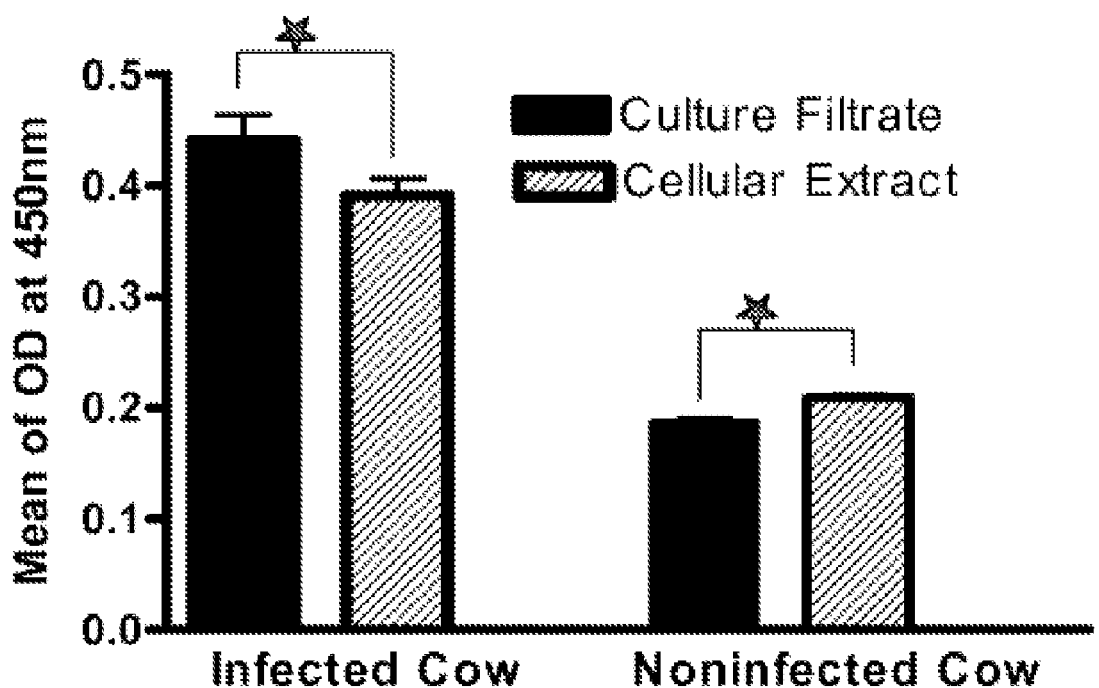
FIG. 4 is a graph showing average ELISA values for culture filtrate (black bars) and cellular extract (diagonally striped bars) from both infected and noninfected cows.
Figure 5:
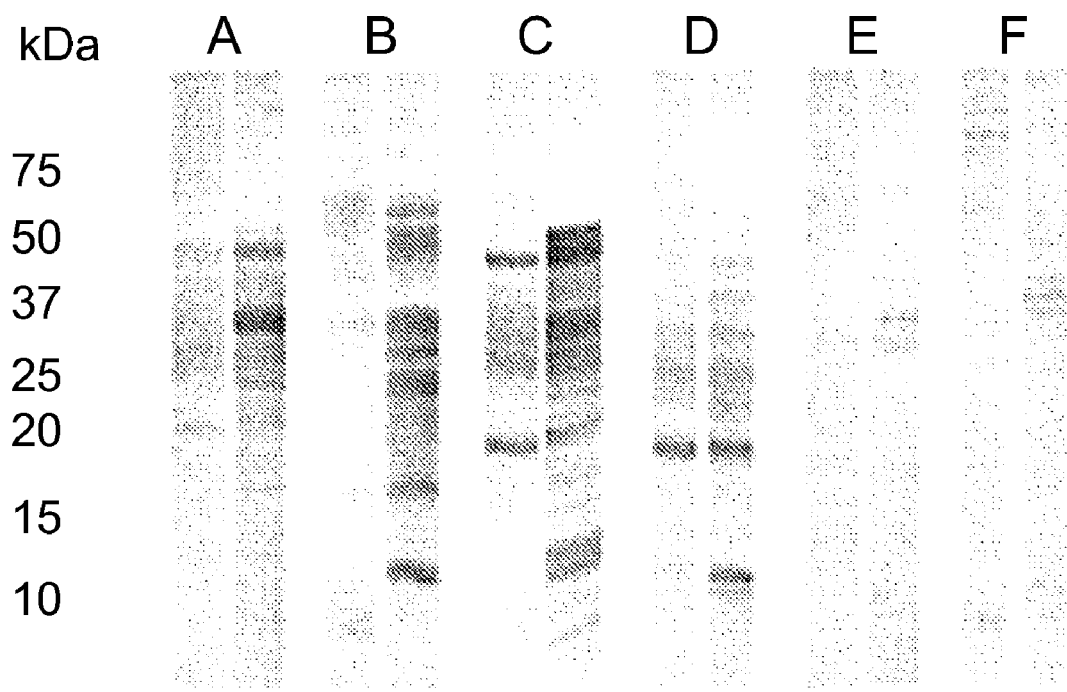
FIG. 5 shows images of compared immunoblots of cellular extract proteins (left lanes) and culture filtrate proteins (right lanes) using sera from 6 infected cattle (A-F).

The following definitions are provided in order to aid the reader in understanding the detailed description of the present invention.

"A", "an", "the" and the like, unless otherwise indicated, include plural forms.

"Antigen" is a substance that evokes an immune response in a subject, especially the production of antibodies. Antigens are usually proteins or polysaccharides foreign to the subject, but may also be any type of molecule, including small molecules (haptens) coupled to a carrier-protein. For example, a *M. paratuberculosis* antigen is a substance that evokes an anti-*M. paratuberculosis* response in a subject, when the subject is immunized with that antigen.

"Antigenic preparation" is a preparation that includes antigens.

"Culture filtrate" (CF) refers to the filtered aqueous phase that is obtained from a growing bacterial culture. Culture filtrate may be obtained by removing the bacterial cells grown in culture, e.g. using centrifugation or filtration. The culture filtrate should preferably be obtained from a bacterial culture that is in early-log growth phase. More preferably, a culture filtrate is obtained from cultured *M. paratuberculosis* strain JTC303. For *M. paratuberculosis* strain JTC303, the early-log phase is approximately 8 to 12 weeks post culture inoculation.

"Antibody" is used in the broadest sense and specifically covers paratuberculosis-specific monoclonal antibodies (including agonist, antagonist, and neutralizing antibodies), paratuberculosis-specific antibody compositions with polyepitopic specificity, single chain paratuberculosis-specific antibodies, and fragments of paratuberculosis-specific antibodies. The antibodies may be anti-*M. paratuberculosis* monoclonal or polyclonal antibodies per se, immunologically effective fragments thereof (e.g., $F_{ab}$, $F_{ab'}$, or $F_{(ab')2}$), or a single chain version of the antibodies, usually designated as $F_v$ regions. Methods of producing polyclonal and monoclonal antibodies, including binding fragments and single chain versions, are well known in the art.

"Immunoglobulin" when used herein refers to a glycoprotein that functions as an antibody. The terms antibody and immunoglobulin may be used interchangeably. Immunoglobulins are found in the blood and tissue fluids, as well as many other body secretions; they take part in an immune response of an organism to bacteria or foreign substances.

Cows that are infected with *M. paratuberculosis* may produce paratuberculosis-specific immunoglobulins. The samples from infected cows may contain immunoglobulins detectable by standard serologic assays, for example through binding with an anti-bovine immunoglobulin-specific antibody. The anti-bovine immunoglobulin-specific antibody can have a detectable label.

"Conjugate" when used herein refers to a detector molecule, such as anti-bovine immunoglobulin-specific antibody, that has been chemically coupled to an indicator system, also called a "label".

"Label" when used herein refers to a detectable compound or composition which is conjugated directly or indirectly to an antibody so as to generate a "labeled" antibody (conjugate). The label may be detectable by itself (e.g. radioisotope label or fluorescent label) or, in the case of an enzymatic label, may catalyze chemical alteration of a substrate compound or composition the product of which is then detectable.

"Subject" as used in this application refers to any human or animal, or to one or more cells derived from a human or an animal. "Subject" refers to any organism classified as a mammal, including humans, domestic and farm animals, and zoo, sports, or pet animals, such as dogs, horses, cats, cattle, pigs, sheep, etc. Preferably, the mammal is human. More preferably, the mammal is bovine.

"Specificity" as used in this application refers to specificity of a diagnostic serological test, and is used as one measure of the test accuracy. The specificity of a paratuberculosis ELISA is the proportion of truly non-*M. paratuberculosis*-infected mammals that yield a negative test result. Diagnostic specificity is generally expressed as a percentage.

"Sensitivity" as used in this application refers to sensitivity of a diagnostic serological test and is used as another measure of the test accuracy. The sensitivity of a paratuberculosis ELISA is the proportion of truly *M. paratuberculosis*-infected mammals that yield a positive test result. In this case, infected mammals are defined as those producing a positive culture test result on antemortem clinical samples, culture being the most widely used reference test for paratuberculosis. Diagnostic specificity is generally expressed as a percentage.

For a given diagnostic assay, specificity and the sensitivity are generally in an inverse relationship based on the assay interpretation cutoff, i.e., the numerical value defining the borderline between negative and positive results. Changing the assay cutoff to increase sensitivity will result in a decrease in specificity.

"ROC" (receiver operating characteristic) curve refers to a method used for the evaluation of tests used in clinical pathology laboratories. The area under the ROC curve is a useful overall measure of test accuracy and may be used to compare different tests or different equipment. The ROC analysis summarizes the diagnostic accuracy of the test, taking into consideration both its specificity and sensitivity (Gardner and Grainer, 2006, *Vet. Clin. Pathol.* 35: 8-17).

This invention provides a *Mycobacterium paratuberculosis* strain JTC303, deposited with the American Type Culture Collection (ATCC) as PTA-7788 on Aug. 15, 2006. Strain JTC303 of *Mycobacterium paratuberculosis* was isolated by the inventors from a sample that originated from a Holstein Bull (#H8122) housed at American Breeders Service (ABS). The sample was ileum (terminal small intestine) tissue.

Mutants of the isolated *Mycobacterium paratuberculosis* strain JTC303 may also be useful for practicing the invention. *M. paratuberculosis* strain JTC303 mutants for the purposes of this invention are mutants whose genomes differ from the parental strain genome by the presence of one, two, three, or more mutations, such as nucleotide changes, deletions, or additions, while still containing a genomic sequence similar to JTC303.

The JTC303 strain may be mutagenized using any random mutagenesis technique known in the art, including, but not limited to, radiation and chemical procedures. Particularly preferred is random chemical mutagenesis, and most preferable is mutagenesis using a suitable agent such as N-methyl-N'-nitro-N-nitrosoguanidine (NTG). General methods for mutagenesis and selection of novel bacterial strains are well known in the art and are described, for example, in Miller, 1992, *A Short Course in Bacterial Genetics*, Cold Spring Harbor Laboratory Press, Cold Spring Harbor, N.Y.; Singer and Berg, 1991, *Genes and Genomes: A Changing Perspective*, University Science Books, Mill Valley, Calif.; Sambrook et al., 1989, *Molecular Cloning: A Laboratory Manual*, 2nd ed., Cold Spring Harbor Laboratory Press, Cold Spring Harbor, N.Y.; and Kaufman et al., 1995, *Handbook of Molecular and Cellular Methods in Biology and Medicine*, CRC Press, Boca Raton, Fla.

In one embodiment, the invention provides novel antigen preparations that may be used in an assay for antibodies to *Mycobacterium paratuberculosis*. Preferably, the antigen preparations are obtained from a mycobacterial culture filtrate. More preferably, the culture filtrate is *Mycobacterium paratuberculosis* JTC303 culture filtrate.

Culture filtrates useful for practicing the invention may be obtained from other mycobacterial strains. Such culture filtrates may be used as antigenic preparations; other culture filtrates may also be combined with the culture filtrate obtained from strain JTC303. Preferably, culture filtrates should be obtained from clinical *M. paratuberculosis* strains, rather than from laboratory-maintained *M. paratuberculosis* strains.

To practice this invention, a skilled artisan will know to use other media compositions, broths, etc., suitable for growth of mycobacteria, in order to obtain an antigenic culture filtrate. These media may be modified, supplemented with various compounds, acidified, etc. Addition of glycerol enhances bacterial growth and yield of antigens. Preferably, the media should be glycerol-based. Existing commercial media may be modified; for example, 7H9 broth (Becton Dickinson, Cockeysville, Md.) may be modified by replacing the glucose with glycerol. This substitution enhances bacterial growth and results in improved yield of antigens. The pH of the media should preferably be kept at 5.5 to 6.5. More preferably, the pH of the media should be kept at about 6.0. In a preferred embodiment, the media for bacterial growth is modified Watson-Reid (WR) broth (formulation described in Sung and Collins, 2003, *Appl. Environ. Microbiol.* 69: 6833-6840) with a pH of about 6.0.

In one example, the culture of *M. paratuberculosis* in an early-log phase is centrifuged to remove (pellet) the bacteria. The remaining aqueous culture filtrate is then concentrated using a size-exclusion filter, preferably a 5,000 molecular weight size-exclusion filter. The culture filtrate may also be dialyzed, e.g. using 10 mM PBS, pH 6.8.

The entire aqueous phase that is obtained from a bacterial culture should be considered a cellular filtrate. For example, if centrifugation of 3,000×g for 10 minutes was used to separate (pellet) the bacteria, then the entire supernatant should be considered culture filtrate.

The culture filtrate may include a variety of antigenic compounds, such as various mycobacterial proteins, carbohydrates, lipids, metabolites, growth factors, etc. The proteins may, for example, be further modified by phosphorylation, glycosylation, and/or acetylation. The compounds in the culture filtrate may be extracellular, secreted, excreted, byproducts of bacterial metabolism, etc. In general, it is only required that the culture filtrate includes compounds that act as antigens and that are necessary to elicit the immune response.

The antigens may be attached to solid support when assays for the detection of an immune response are performed. For example, the antigens may be used for coating microplate wells for enzymatic-based assays such as ELISA, although there are many other comparable technologies for detection of antigen-antibody interactions. These include, for example, radioimmunoassay, agar-gel immunodiffusion, agglutination, complement fixation, etc.

In one embodiment, samples such as serum or milk are mixed with absorbing antigens prior to contacting the sample with the *M. paratuberculosis* antigens. The absorbing antigens are mixed to absorb the nonspecific antibodies in the sample. The absorbing antigens may be added in the form of an absorbing antigen preparation. These absorbing antigens may be from one type of mycobacteria. Alternatively, they may be from multiple different mycobacteria. Preferably, the absorbing antigens are from *Mycobacterium* terse or *Mycobacterium phlei*. The antigens are cellular extracts of these organisms and are used at a final concentration of about 250 micrograms per milliliter of diluted sample, the recommended sample dilution being 1:50.

In another embodiment, the invention provides an antibody that specifically binds to any of the above or below described antigens. This is a paratuberculosis-specific antibody. Optionally, the antibody is a monoclonal antibody, humanized antibody, antibody fragment, or single-chain antibody. The paratuberculosis-specific antibody is capable of binding to the antigen, creating an antigen-antibody complex.

Once an antigen-antibody complex is formed, a second antibody or comparable detection molecule is used to detect the presence of the first paratuberculosis-specific antibody. The antigen-antibody complex is brought together with the second antibody which binds to the first antibody. The antigen-antibody complex may be attached to solid support. The unbound sample components are then removed. Alternatively, the antigen-antibody complex may be separated from the other serum components prior to binding of the second antibody, using standard separation techniques. After such a separation/purification step, the second antibody is then used to detect the presence of the first antibody. Alternatively, a non-antibody molecule that binds to immunoglobulins is used to detect the paratuberculosis-specific antibody. Examples of such molecules include Protein A and Protein G.

The second antibody may be labeled with a label, for example, a bead, a radioisotope, a ligand, a chemiluminescent molecule, a dye, a fluorescent molecule, or an enzyme. Labeled antibodies and reagents useful in immunoassays are disclosed in U.S. Pat. No. 4,490,473.

Radioactive labels such as iodine-125 ($^{125}$I) or other radioactive elements may be applied by known procedures. Techniques for labeling antibodies with $^{125}$I or other radioactive labels are described in Greenwood et al., 1963, *Biochem. J.* 89: 114-123; Harlow and Lane, 2006, *Labeling Antibodies with Iodine*, Cold Spring Harbor Protocols, 2006: pdb.prot4287.

Fluorescent labels and procedures for coupling them to antibodies are described in U.S. Pat. Nos. 4,256,834 and 4,261,968. Labeled secondary antibody conjugates are known, and may include labeled biotin-binding proteins for detection of biotinylated targets, fluorophore-labeled Protein A and G conjugates, gold conjugates, and the zenon antibody labeling technology (Invitrogen, Carlsbad, Calif.).

A wide variety of enzymatic labels may be applied, and these are selected in conjunction with the substrate to be used in the analysis by procedures well-known in the art. For example, enzymes such as alkaline phosphatase, horseradish peroxidase, catalase, peroxidase, betaglucuronidase, glucose-6 phosphate dehydrogenase, urease, phosphatase, and glucose oxidase are conveniently linked to antibodies by art recognized techniques such as those described in U.S. Pat. Nos. 3,875,011, 3,791,932 and 3,879,262. Preferably, the immunoglobulin-specific antibody of the present invention or suitable alternative is labeled using the biotin-avidin labeling method, which is widely used for enzyme immunoassays.

Alternatively, the binding of second antibody may be inferred by the adherence of the complex to a solid surface to which this second antibody is adherent, or by the ability of the complex to activate the complement components in sera, or by other means known in the art.

This invention also relates to an in vitro assay method for the detection of *M. paratuberculosis*-induced immune responses. Thus, a method of detecting an immune response to paratuberculosis-specific antigens in a mammal, preferably bovine, is provided. The method includes growing cultures of *M. paratuberculosis* strain JTC303, removing bacterial cells from the aqueous phase of the culture and concentrating the resulting product to obtain an antigenic culture filtrate, incubating a sample from the mammal with the culture filtrate, and detecting the presence of antibodies in the sample to indicate an immune response to the paratuberculosis-specific antigens.

The assay format may be Western blot, radioimmunoprecipitation, radioimmunoassay (RIA), or an enzyme-linked immunosorbent assay (ELISA), including a sandwich ELISA. In one aspect, an assay, named JTC-ELISA, utilizes the JTC303 culture filtrate antigens of the present invention for the detection of bovine antibodies in serum using an enzyme-linked immunosorbent assay (ELISA) format.

The method may employ a solid support such as a column, a dipstick, a filter or a microtiter dish. The ELISA may include detection of an antibody that binds to a paratuberculosis-specific antigen using a labeled anti-Ig antibody. The antigen used in the practice of the method may be obtained from *M. paratuberculosis* JTC303. Preferably, the antigen may be obtained from *M. paratuberculosis* JTC303 culture filtrate. The ELISA also may be a competitive assay. The assay may involve quantification. The assay may also be automated, and may, for example, be run on standard ELISA automated plate readers.

Detection of a paratuberculosis-specific immune response in a subject may be performed using various samples, including serum or milk obtained from a subject. The subject sampled may be a mammal; preferably, the mammal is human or animal, e.g. bovine.

The present invention thus provides novel diagnostic tests for paratuberculosis, Johne's disease, Crohn's disease, and related intestinal diseases.

The JTC-ELISA may be used with a variety of samples that contain antibodies to the target pathogen (*M. paratuberculosis*), including whole blood sample, serum, milk, fecal samples, or other clinical samples.

In some preferred embodiments, ELISA may be conducted after serum preabsorption. The serum preabsorption may be performed using cellular extract proteins. These cellular extract proteins can be obtained from mycobacteria, such as, for example, from homogenized *Mycobacterium phlei* or *Mycobacterium terrae.*

With minor modification of reagents, such as the conjugate system, the JTC-ELISA may be used for the detection of paratuberculosis-specific antibodies in animal species other than cattle. These mammalian species may include goats, sheep, bison, llamas and other ruminants and pseudoruminants as well as humans and nonhuman primates.

The present invention also relates to a kit for the detection of *M. paratuberculosis*-induced immune responses. The kit includes an antigen that binds immunologically to a paratuberculosis-specific antibody (Ig) from a provided sample. The kit may include an antigen obtained from *M. paratuberculosis* culture filtrate. Preferably, the culture filtrate may be obtained from *M. paratuberculosis* strain JTC303. The kit may also include an anti-bovine Ig antibody.

When sample from an infected cow is contacted with the antigen, the bovine immunoglobulin (Ig) antibody binds to the antigen and forms an antigen antibody (Ig) complex. The anti-bovine Ig antibody is used for detection of the presence of the paratuberculosis-specific antibody (immunoglobulin) in the provided sample. The anti-bovine Ig antibody may be labeled, for example, with a bead, a radioisotope, a ligand, a chemiluminescent molecule, a fluorescent molecule, an enzyme, or with another detectable conjugate. The detection of the anti-bovine Ig antibody can be quantitative.

In alternatively preferred embodiments, the anti-immunoglobulin antibody is directed toward the immunoglobulin of the species from which the specimen to be tested was obtained. For example, when testing specimens obtained from human subjects, the anti-immunoglobulin antibody is anti-human Ig antibody.

In one embodiment, the present invention relates to an ELISA diagnostic kit for the assay of *M. paratuberculosis* antibodies in a sample obtained from a *bovid* (cow). Preferably, the ELISA kit includes an antigen from *M. paratuberculosis* strain JTC303 and an anti-bovine Ig antibody, which may be labeled.

The kit may be used for diagnosing mammalian samples such as serum or milk. In comparison to the tested commercial ELISA kits, the JTC-ELISA significantly reduces the background noise. Because the background noise of the JTC-ELISA is relatively low, a skilled artisan may further improve the signal-to-noise ratio of the diagnostic test by amplifying the signal coming from the label. In a preferred embodiment, the biotin-avidin labeling method may be used for antibody signal amplification.

EXAMPLES

It is to be understood that this invention is not limited to the particular methodology, protocols, subjects, or reagents described, and as such may vary. It is also to be understood that the terminology used herein is for the purpose of describing particular embodiments only, and is not intended to limit the scope of the present invention, which is limited only by the claims. The following examples are offered to illustrate, but not to limit the claimed invention.

Example 1

Obtaining Antigens from *M. paratuberculosis*

Antigens from *M. paratuberculosis* were evaluated as candidates for development of serodiagnostic assays for bovine paratuberculosis. The bacterial strains tested were *Mycobacterium paratuberculosis* JTC303, ATCC 19698, K10, and JTC114.

The culture media used were Middlebrook 7H (7H9) broth (Becton Dickinson, Cockeysville, Md.) and modified Watson-Reid (WR) broth supplemented with 0.0002% (wt/vol) Mycobactin J (Allied Monitor, Fayetteville, Mo.). The pH of the modified WR medium was adjusted to a value of 6.0.

Antigens were obtained from homogenized cells (cellular extract, CE), or from culture filtrate (CF). Typically, the CF was concentrated approximately 40-fold.

Protein expression profiles and antigenicity of culture filtrates (CF) and cellular extracts (CE) of *Mycobacterium paratuberculosis* were compared by SDS-PAGE, 1-dimensional electrophoresis (1-DE) and 2-dimensional electrophoresis (2-DE) immunoblots, and ELISA. The CE proteins were extracted by mechanical disruption of cells using glass beads and a high speed agitator. The CF proteins were harvested from supernatants of stationary phase liquid cultures and concentrated by size-exclusion filtration.

Antigenicity of CF and CE proteins was first determined by 1-DE and 2-DE immunoblots using serum from a cow naturally infected with *M. paratuberculosis*.

The CE protein profiles differed depending on which culture medium was used to grow *M. paratuberculosis* (WR vs. 7H9), as previously reported (Sung and Collins, 2003, *Appl. Environ. Microbiol.* 70: 1688-1697). FIG. 1 shows an SDS-PAGE image of *M. paratuberculosis* cellular extract proteins for bacteria cultured in Watson-Reid media (lane 1), cultured in 7H9 media (lane 2), and from culture filtrate proteins for bacteria cultured in Watson-Reid media (lane 3). Molecular masses are indicated on the left of the gel in kilodaltons (kDa). CF antigens produced from early log-phase cultures of *M. paratuberculosis* grown in WR medium are preferred.

Immunoblots highlighted the antigenic disparity between CE and CF proteins. As shown in FIG. 2, proteins from the culture filtrate (CF; lane 3) reacted more strongly with serum from infected cattle than did cellular extract (CE) proteins (lane 1 and 2). Weak staining and few bands appeared after immunoblotting for CE proteins produced from *M. paratuberculosis* grown in WR or 7H9 media. This was even more evident after serum preabsorption using *M. phlei* cellular extract proteins (panel B).

The 2-DE immunoblots of CE and CF preparations were done with and without serum absorption with *M. phlei* CE proteins. Total staining intensity of all proteins was determined and compared by image analysis software. The total immunoreactivity of serum from a *M. paratuberculosis* infected cow was stronger to CF than CE proteins, in agreement with the results of 1-DE immunoblots.

Serum absorption with *M. phlei* CE proteins markedly decreased the number of immunoreactive spots for both CE and CF antigens, but the effect was greater for CE proteins than for CF proteins. Some CF proteins showed the same immunoblot staining intensity with or without serum absorption.

Differences were observed between the proteins from the culture filtrate in comparison to the cellular extract proteins. Image analysis of 23×30 cm 2-DE gels resolved approximately 400 CE and 240 CF proteins (FIG. 3). As shown in FIG. 3, CE proteins were relatively evenly distributed by mass and pI on a two-dimensional IEF SDS-PAGE (2-DE) gel (A). In contrast, most CF proteins (B) were <37 kDa and had acidic pI values (pH 4.0 to pH 5.5). Several proteins appeared as strings of spots of similar mass but different pIs suggesting the existence of proteins modified by phosphorylation, glycosylation, or acetylation.

The sera from 444 naturally *M. paratuberculosis*-infected and 412 infection-free cattle were tested by ELISA using cellular extract (CE) and culture filtrate (CF) proteins as the solid-phase antigens (FIG. 4). CE or CF (1 μg/ml) was used as the solid-phase antigen. The serum reacted strongly to more proteins in the CF than the CE. Mean ELISA OD for CE (diagonally striped bars) and CF (black bars) antigens was significantly different ($p<0.0169$ and $p<0.001$) for infected and infection-free cattle, respectively. Receiver-operator characteristic (ROC) curves analysis of ELISA results showed a significantly greater area under the curve for CF compared to CE ($p<0.05$).

Antigenicity of the culture filtrate and the cellular extract was directly compared in some experiments. An immunoblot analysis was conducted with six sera randomly chosen from the population of more than 400 sera from *M. paratuberculosis*-infected cattle. FIG. 5 shows immunoblots of the six tested sera (A-F) from six *M. paratuberculosis*-infected cattle after absorption with cellular extract of *M. phlei*. The immunoblots were developed with 3,3'-Diaminobenzidine tetrahydrochloride. Immunoblots of CE proteins (left lanes in A-F) and CF proteins (right lanes in A-F) showed stronger reactivity to CF proteins.

The culture filtrates were found to have more immunogenic proteins than cellular extracts, indicating that serologic tests for bovine paratuberculosis may be improved by use of proteins derived from CF instead of CE.

Analysis of SDS-PAGE gels showed that the majority of CF proteins were low molecular weight (<50 kDa) in contrast to those from CE which were evenly distributed in size up to 100 kDa. By 2-DE, CF proteins had a narrow range of pI values with most being between pH 4.0 and 5.5 whereas CE proteins had pI values evenly distributed from pH 4.0 to 7.0.

Example 2

Comparison of CF Antigens from *M. paratuberculosis* Strains

The antigenicity of the culture filtrate obtained from JTC303 was compared to the antigenicity of the culture filtrate obtained from other strains, and to a newer commercially available kit (IDEXX Laboratories, Inc., Westbrook, Me.).

For this experiment, 44 samples of non-infected cows were selected out of a repository of 412 non-infected cows. In addition, 48 samples of *M. paratuberculosis*-infected cows out of a repository of 444 infected cows were tested. The summary of the ELISA results for culture filtrate antigens is shown in Table 1. The area under the ROC curve is much larger for the JCT303 antigens, indicating superiority of this test over the others tested.

TABLE 1

Comparison of CF antigens from different *M. paratuberculosis* strains ELISA results

|  | IDEXX kit | | JTC303 2 month* | | JTC114 2 month | | ATCC19698 2 month | |
| --- | --- | --- | --- | --- | --- | --- | --- | --- |
| Cut-off | 0.032 | 0.146 | 0.07 | 0.0744 | 0.022 | 0.067 | 0.075 | 0.079 |
| Sensitivity | 41.67 | 22.92 | 70.83 | 68.75 | 50 | 35.42 | 43.75 | 43.75 |
| Specificity | 97.73 | 100 | 97.73 | 100 | 97.73 | 100 | 97.73 | 100 |
| Area under ROC curve | 0.7992 | | 0.9335 | | 0.7069 | | 0.7981 | |

*2 months indicates culture age at antigen harvest, which approximates early log phase growth.

Example 3

Comparison of ELISA Tests

A novel ELISA for bovine paratuberculosis (JTC-ELISA) was developed and evaluated using a panel of well characterized bovine sera. This new ELISA is based on secreted *Mycobacterium paratuberculosis* antigens and absorption of sera by *Mycobacterium phlei* antigens. Analytical sensitivity of the JTC-ELISA is enhanced using a commercial avidin-biotin conjugate system.

The JTC-ELISA was evaluated on a panel of previously described bovine sera (Collins et al., 2005, *Clin. Diagn. Lab. Immunol.* 12: 685-692). Paratuberculosis cases (n=444) were fecal culture-positive cows and the controls (n=412) were cows resident in seven Midwest dairy herds free of paratuberculosis: test-negative for more than 4 years, i.e., level 4 in the Voluntary Bovine Johne's Disease Program.

JTC-ELISA results were compared to those produced with paratuberculosis ELISA kits sold by IDEXX (IDEXX Laboratories, Inc., Westbrook, Me.), CSL/Biocor (CSL/Biocor, Omaha, Nebr.), Institut Pourquier (Institut Pourquier, Montpellier, France), and Synbiotics (Synbiotic Corp., San Diego, Calif.) by ROC (receiver operating characteristic curves) analysis. ELISA sensitivity, specificity, and area under the ROC curve are tabulated below.

In comparative tests, the JTC-ELISA achieved a diagnostic sensitivity of over 50% for detecting and identifying dairy cattle infected with and shedding *Mycobacterium paratuberculosis* in their feces that was significantly larger than that of the tested existing commercial ELISA kits, while retaining a high diagnostic specificity (over 97%), with the area under the ROC curve being superior to the tested existing commercial kits (see Table 2).

These data show that JTC-ELISA has significantly higher diagnostic sensitivity, with equivalent specificity, compared to four other widely used commercial ELISA kits for bovine paratuberculosis.

TABLE 2

Comparison of ELISA kits

| Kit/Assay | Sensitivity (95% C.I.) | Specificity (95% C.I.) | Area Under ROC Curve (95% C.I.) |
| --- | --- | --- | --- |
| IDEXX | 28.9% (24.5-33.5) | 95.3% (92.53-97.22) | 0.619 (0.580-0.659) |
| CSL/Biocor | 28.4% (24.5-33.1) | 99.7% (98.46-99.99) | 0.795 (0.741-0.808) |
| Pourquier | 28.0% (23.7-32.5) | 100.0% (99.98-100.00) | 0.709 (0.673-0.745) |
| Synbiotics | 44.5% (39.3-50.8) | 84.9% (80.48-88.46) | 0.706 (0.666-0.747) |
| JTC-ELISA | 56.3% (51.6-61.0) | 99.0% (97.50-99.70) | 0.894 (0.873-0.915) |

C.I. = 95% confidence interval

It is to be understood that this invention is not limited to the particular devices, methodology, protocols, subjects, or reagents described, and as such may vary. It is also to be understood that the terminology used herein is for the purpose of describing particular embodiments only, and is not intended to limit the scope of the present invention, which is limited only by the claims. Other suitable modifications and adaptations of a variety of conditions and parameters, obvious to those skilled in the art of diagnostic assays, are within the scope of this invention. All publications, patents, and patent applications cited herein are incorporated by reference in their entirety for all purposes.

What is claimed is:

1. A method of detecting an immune response to a *M. paratuberculosis* strain JTC303-specific antigen in a subject, comprising the steps of:
    (a) absorbing nonspecific antibodies in a sample from the subject using a *Mycobacterium* cellular extract,
    (b) contacting the sample from the subject with a culture filtrate obtained from *M. paratuberculosis* strain JTC303, and
    (c) detecting the presence of an antigen-bound antibody in the sample to indicate an immune response to the paratuberculosis-specific antigen.

2. The method of claim 1 wherein the cellular extract is from *M. phlei* or *M. terse*.

3. The method of claim 1 wherein step (b) comprises using an enzyme-linked immunosorbent assay (ELISA).

4. The method of claim 3 wherein the ELISA has a sensitivity of at least 50%, while having a specificity of at least 97%.

5. The method of claim 3 wherein the subject is human.

6. The method of claim 3 wherein the subject is bovine.

7. The method of claim 3 wherein the sample is serum.

8. The method of claim 3 wherein the sample is milk.

* * * * *

UNITED STATES PATENT AND TRADEMARK OFFICE
CERTIFICATE OF CORRECTION

PATENT NO. : 8,158,371 B2  
APPLICATION NO. : 12/904790  
DATED : April 17, 2012  
INVENTOR(S) : Collins et al.

Page 1 of 1

It is certified that error appears in the above-identified patent and that said Letters Patent is hereby corrected as shown below:

Column 6, line 24 "terse" should read --terrae--

Column 12, line 53 "M. terse" should read --M. terrae--

Signed and Sealed this
Thirty-first Day of July, 2012

David J. Kappos
*Director of the United States Patent and Trademark Office*